United States Patent
DiBenedetto

(10) Patent No.: US 9,445,839 B2
(45) Date of Patent: *Sep. 20, 2016

(54) UTERINE CLAMP FOR TREATING POSTPARTUM HEMORRHAGE AND FACILITATING UTERINE REPAIRS

(71) Applicant: Robert J. DiBenedetto, Boonton, NJ (US)

(72) Inventor: Robert J. DiBenedetto, Boonton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/865,018

(22) Filed: Sep. 25, 2015

(65) Prior Publication Data

US 2016/0166283 A1  Jun. 16, 2016

Related U.S. Application Data

(63) Continuation of application No. 14/570,093, filed on Dec. 15, 2014, now Pat. No. 9,168,061.

(51) Int. Cl.
*A61B 17/42* (2006.01)
*A61B 17/44* (2006.01)
(Continued)

(52) U.S. Cl.
CPC .......... *A61B 17/4241* (2013.01); *A61B 17/122* (2013.01); *A61B 17/2812* (2013.01); *A61B 17/44* (2013.01); *A61B 2017/12004* (2013.01); *A61B 2017/4216* (2013.01)

(58) Field of Classification Search
CPC .......... A61B 17/42; A61B 2017/4216; A61B 2017/4225; A61B 17/4241; A61B 17/44; A61B 2017/445; A61B 2017/447; A61B 17/122; A61B 10/06; A61B 2017/1125; A61B 17/28; A61B 17/29; A61B 2017/2926; A61B 2017/2945; A61B 17/0483; B25B 7/04; B25B 7/10; B25B 7/08; B25B 7/02; B25B 3/00; B25B 5/00; B25B 5/003; B25B 5/067; B25B 5/082; B25B 5/101; B25B 5/125; B25B 5/14; B25B 5/147; B25B 7/123; B25B 13/40; B25B 13/56; B25B 17/00
See application file for complete search history.

(56) References Cited

U.S. PATENT DOCUMENTS 1,007,824 A  11/1911  Trosper
3,364,919 A  1/1968  Hunnicutt
(Continued)

FOREIGN PATENT DOCUMENTS

CN  2050313 U  1/1990
CN  2265162 Y  10/1997
(Continued)

OTHER PUBLICATIONS

B-Lynch, C., et al., "The B-Lynch Surgical Technique for the Control of Massive Postpartum Hæmorrhage: An Alternative to Hysterectomy? Five Cases Reported," British Jour. of Obstetrics and Gynæcology, vol. 104 (Mar. 1997), pp. 372-375.
(Continued)

*Primary Examiner* — Jonathan Miles
(74) *Attorney, Agent, or Firm* — David M. Quinlan, P.C.

(57) ABSTRACT

A medical clamp for holding a uterus includes a first and second curved plates that capture between them the major exterior walls of the uterus, and an operating handle having pivotally connected first and second actuating arms, each of which has a distal portion and a proximal portion with a grip for a user, whereby the distal portions are moved toward each other when the user moves the grips toward each other to capture the uterus between the plates. Ball-and-socket joints connect the distal handle portions of the actuating arms to respective plates. The ball-and socket joints enable rapid positioning of the clamp on the uterus to arrest emergency postpartum hemorrhaging, assist in exerting pressure on the uterus over the entire extent of the plates, facilitate manipulation of the uterus using the clamp, and permit other surgical interventions to be performed with the clamp in place.

27 Claims, 4 Drawing Sheets

(51) Int. Cl.
*A61B 17/28* (2006.01)
*A61B 17/122* (2006.01)
*A61B 17/12* (2006.01)

(56) References Cited

U.S. PATENT DOCUMENTS

| | | | |
|---|---|---|---|
| 4,075,749 | A | 2/1978 | Hubeny |
| 4,170,125 | A | 10/1979 | Minka |
| 4,223,673 | A | 9/1980 | Harris |
| 5,022,291 | A | 6/1991 | McBain |
| 5,143,359 | A | 9/1992 | Bush |
| 5,722,647 | A | 3/1998 | Rattaro et al. |
| 6,099,539 | A | 8/2000 | Howell et al. |
| 6,220,126 | B1 | 4/2001 | Domenge |
| 6,315,780 | B1 | 11/2001 | Lalonde |
| 6,676,680 | B1 | 1/2004 | Packer |
| 6,905,506 | B2 | 6/2005 | Burbank et al. |
| 7,220,252 | B2 | 5/2007 | Shah |
| 7,354,444 | B2 | 4/2008 | Burbank et al. |
| 7,404,821 | B2 | 7/2008 | Burbank et al. |
| 7,594,890 | B2 | 9/2009 | Burbank et al. |
| 7,651,511 | B2 | 1/2010 | Burbank et al. |
| 8,579,925 | B2 | 11/2013 | Staggs |
| 2001/0015561 | A1 | 8/2001 | Tseng |
| 2002/0111537 | A1 | 8/2002 | Taylor et al. |
| 2002/0116025 | A1 | 8/2002 | Haab |
| 2007/0142860 | A1 | 6/2007 | Kotmel et al. |
| 2012/0047714 | A1 | 3/2012 | Barillaro et al. |
| 2012/0172898 | A1 | 7/2012 | Pedrick et al. |

FOREIGN PATENT DOCUMENTS

| | | |
|---|---|---|
| CN | 20101055393 Y | 5/2008 |
| CN | 202342111 U | 7/2012 |
| CN | 202426595 U | 9/2012 |
| CN | 202458535 U | 10/2012 |
| CN | 203074796 U | 7/2013 |
| EP | 2404562 | 11/2012 |
| JP | 10234745 | 9/1998 |
| KR | 20010002164 | 1/2001 |
| KR | 100904045 | 6/2009 |

OTHER PUBLICATIONS

Chez, R.A., et al., "Clinical Dialogue: The B-Lynch Suture for Control of Massive Postpartum Hemorrhage," Contemporary OB/GYN, Aug. 1998, pp. 93-98.

Cho, J.H., et al., "Instruments & Methods—Hemostatic Suturing Technique for Uterine Bleeding During Cesarean Delivery," Obstetrics & Gynecology, vol. 96, No. 1 (Jul. 2000), pp. 129-131.

Hayman, R.G., et al., "Uterine Compression Sutures: Surgical Management of Postpartum Hemorrhage," Obstetrics & Gynecology, vol. 99, No. 3 (Mar. 2002), pp. 502-506.

An, G.H., et al., "Outcomes of Subsequent Pregnancies After Uterine Compression Sutures for Postpartum Hemorrhage," Obstetrics & Gynecology, vol. 122, No. 3 (Sep. 2013), pp. 565-570.

Ochoa, M. et al., "Pyometria After Hemostatic Square Suture Technique," Obstetrics & Gynecology, vol. 99, No. 3 (Mar. 2002), pp. 506-509.

O'Leary, J.L, et al., "Uterine Artery Ligation in the Control of Intractable Postpartum Hemorrhage," American Jour. of Obstetrics & Gynecology, vol. 94, No. 7 (Apr. 1, 1966), pp. 920-924.

O'Leary, J.L, et al., "Uterine Artery Ligation for Control of Postcaesarean Section Hemorrhage," Obstetrics & Gynecology, vol. 43, No. 6 (Jun. 1974), pp. 849-853.

O'Leary, J.L., "Uterine Artery Ligation for Control of Postcaesarean Section Hemorrhage," The Jour. of Reproductive Medicine, Inc., vol. 40, No. 3 (Mar. 1995), pp. 189-193.

Roman, A.S., et al., "Seven Ways to Control Postpartum Hemorrhage," Contemporary OB/GYN (Mar. 2003), pp. 34-48, 53.

Stitely, M.L., et al. "Obstetric Emergencies: Postpartum Hemorrhage—Solutions to 2 Intractable Cases," OBG Management (Apr. 2007), pp. 64-76.

"Postpartum Hemorrhage: ACOG Practice Bulletin—Clinical Management Guidelines for Obstetrician-Gynecologists, No. 76, Oct. 2006," Obstetrics & Gynecology, vol. 108, No. 4 (Oct. 2006), pp. 1-9.

Uterine Atony Device, University of Virginia, 2009 (various Internet sources).

Uterine Compression Clamp Immediately Slows Hemorrhage Rate, Original Press release by Symmetry Medical, Inc., Jun. 26, 2012.

"Sequential Steps in Managing Postpartum Hemorrhage," UpToDate, http://www.update.com/contents/image?Key=OBGYN%2F57307&rank=1 . . . , Wolters Kluwer Health, last visited Nov. 5, 2013.

UTERINE CLAMP FOR TREATING POSTPARTUM HEMORRHAGE AND FACILITATING UTERINE REPAIRS

BACKGROUND OF THE INVENTION

1. Field of the Invention

The present invention relates to a device for clamping a uterus, and more particularly, to a medical clamp for compressing a uterus to achieve immediate cessation of blood loss from postpartum hemorrhage and provide sufficient time for other interventions that can promote permanent hemostasis and/or for securely grasping a uterus to permit a surgeon to readily position it to facilitate postpartum repairs such as suturing a caesarean incision.

2. Description of Related Art

During pregnancy the placenta implants itself into the internal wall of the uterus and is naturally expelled after delivery. The placenta is rich in blood vessels intimately interconnected with blood vessels in the uterine wall. Accordingly, when the uterus sheds the placenta post-delivery there is a potential for severe and rapid hemorrhaging. In normal childbirth the uterine walls, which are heavily muscled, firmly contract upon themselves and achieve hemostasis in a short time. Uterine atony, in which the uterus fails to contract on its own after delivery, is one cause of a critical event known as postpartum hemorrhaging (PPH). If PPH occurs the mother can lose massive amounts of blood in a very short time, and hemorrhaging due to conditions such as atony is a leading cause of death incident to childbirth. Another example of an abnormal condition that can cause PPH is as retained placenta. An example of this condition is placenta accreta, in which the placenta implants itself too deeply into the uterine wall during pregnancy. This can cause portions of the placenta to remain attached to the uterine wall instead of being shed in the normal fashion, which can result in excessive bleeding at the site of the placental invasion into the uterine wall.

The medical literature describes a number of ways to treat PPH. One favored approach is the administration of so-called uterotonic drugs, that is, compounds known to promote uterine contractions, examples being oxytocin or prostaglandins such as misoprostol. Drug therapy is sometimes accompanied by manual massage of the uterus to encourage contraction and by transfusions to replace lost blood. Another technique is packing the uterus with gauze, which can be impregnated with a clotting agent such as thrombin. Generally, these techniques are tried before surgical interventions. The literature discusses these and numerous other types of interventions. See, for example, Hayman, R. G., et al., "Uterine Compression Sutures: Surgical Management of Postpartum Hemorrhage," *Obstetrics & Gynecology*, Vol. 99, No. 3 (March 2002), pp. 502-506; Roman, A. S., et al., "Seven Ways to Control Postpartum Hemorrhage," *Contemporary OB/GYN* (March 2003), pp. 34-48; "Postpartum Hemorrhage: ACOG Practice Bulletin—Clinical Management Guidelines for Obstetrician-Gynecologists, Number 76, October 2006," *Obstetrics & Gynecology*, Vol. 108, No. 4 (October 2006), pp. 1039-1047; and Stitely, M. L., et al. "Obstetric Emergencies: Postpartum Hemorrhage—Solutions to 2 Intractable Cases," *OBG Management* (April 2007), pp. 64-76. All of the descriptions of PPH intervention protocols and procedures described in these publications are incorporated herein by reference. Drug therapy is the most preferred initial intervention, and in many if not most cases proves effective in achieving hemostasis. While drug therapy is widely used in first-world countries, the required drugs are often not available in less developed areas of the world.

If drugs do not cause the uterus to contract spontaneously, or are unavailable, and related therapies such as massage and/or packing fail to achieve hemostasis, surgical intervention is usually indicated. The most effective intervention in the presence of uncontrolled PPH is a hysterectomy, but this is regarded more or less as a last resort since it permanently prevents further childbearing and requires an extended post-operative recovery period. One type of non-radical surgical intervention seeks to stanch the flow of blood to the uterus through arterial ligation or selective arterial embolization. Other more complex interventions include suturing the uterus in various ways to compress the uterine walls together. One such intervention is the B-Lynch technique, so-called after its inventor Christopher B-Lynch. It is described in some of the literature references mentioned above, and in more detail in B-Lynch, C., et al., "The B-Lynch Surgical Technique for the Control of Massive Postpartum Hæmorrhage: An Alternative to Hysterectomy? Five Cases Reported," *British Jour. of Obstetrics and Gynæcology*, Vol. 104 (March 1997), pp. 372-375. The descriptions in this article of suturing procedures used in the presence of PPH are incorporated herein by reference.

FIGS. 1 to 3 illustrate a basic version the B-Lynch technique. FIG. 1 is an anterior view of a uterus U that has been exteriorized via a laparotomy after a vaginal delivery and an incision IN has been made in the lower uterine segment. If delivery was via caesarean section (sometimes referred to herein as a "C-section"), the uterus with the incision IN will be exposed as shown in FIG. 1. The B-Lynch suture is begun by passing the needle NE and a suitable suturing material through the uterus's anterior major wall AW at a first puncture P1 about three cm from the right side and about 3 cm below the edge of the incision IN. The needle is passed through the uterine cavity to emerge at a second puncture P2 in the anterior wall approximately in line with the puncture P1 and about three cm above the incision IN. The suture is drawn up the exterior of the anterior wall AW to provide a right-side anterior traverse RTA, over the top of the fundus of the uterus, and then down the exterior of the posterior major wall PW to provide a right-side posterior traverse RTP, shown in FIG. 2. ("Right" and "left" are from the patient's perspective; the surgeon in this example stands on the patient's left side.) The surgeon then passes the needle through the posterior uterus wall at a third puncture P3 at the site of the incision IN and then back to the posterior side of the uterus through a puncture P4. The suture is then drawn up the exterior of the posterior wall PW to provide a left-side posterior traverse LTP, shown in FIG. 2, over the top of the fundus of the uterus, and then down the exterior of the anterior wall AW to provide a left-side anterior traverse LTA, shown in FIG. 1. The surgeon passes the needle through the anterior wall AW at a fifth puncture P5 about three cm from the left side and about 3 cm above the edge of the incision IN. The needle is passed through the uterine cavity to emerge at a sixth puncture P6 approximately in line with the puncture P5 and about three cm below the incision IN. (In the description herein, the term "fundus" refers generally to the portion of the uterus in which the fetus grows, and "lower uterine segment" refers generally to the portion of the uterus leading from the fundus to the cervix, although those skilled in the art will appreciate that these terms are for convenience of description and are not meant to limit the scope of the claimed subject matter in any way.)

With the suture in place as shown in FIGS. 1 and 2, the ends of the suture extending from the punctures P1 and P6 are pulled tight. This requires an assistant to compress the anterior and posterior walls of the uterus together as the surgeon tightens the suture. Otherwise, the uterus may not fold on itself in the desired manner (with the anterior and posterior major walls compressed together) or the suture may break. If hemostasis is satisfactorily achieved, the surgeon throws a knot KN around the lower uterine segment with the ends of the suture, preferably followed by two or three additional throws for additional security. The incision IN is then sutured closed. FIG. 3 shows the uterus after the application of the B-Lynch technique.

Although this technique is generally effective in achieving hemostasis of a hemorrhaging uterus, its complexity can potentially be a serious shortcoming. In cases of severe PPH the passage of seconds can mean the difference between life and death of the patient. During PPH, the patient's abdominal cavity rapidly fills with blood and her vital signs weaken at a rate that even experienced physicians can find alarming and stress-producing. One surgeon has been quoted as saying, "To me, there is one obstetrical complication of which I must admit to actual panic: that complication is postpartum hemorrhage . . . . I have known men far more experienced than I, to be so completely unnerved in its presence that clear, sound judgment is lost." O'Leary, J. L., et al., "Uterine Artery Ligation in the Control of Intractable Postpartum Hemorrhaging," *American Jour. of Obstetrics &. Gynecology*, Vol. 94, No. 7 (April 1966), pp. 920-924 (quoted in Weekes, L., et al., *American Jour. of Obstetrics & Gynecology*, Vol. 71, No. 1, pp. 45-50 (1956)). The descriptions in this article of arterial ligation procedures used in the presence of PPH are incorporated herein by reference. As for B-Lynch procedures, they can take vital seconds to implement, and surgeons, particularly those with insufficient experience in using these procedures, may not be able to achieve hemostasis in time to save the patient or preclude more radical interventions such as hysterectomy. Although certain modifications intended to simplify the classic B-Lynch technique are described in the literature, see Hayman, R. G., et al., "Uterine Compression Sutures: Surgical Management of Postpartum Hemorrhage," cited above, they still may be too complicated for an inexperienced surgeon to implement in time to save the patient or preempt a hysterectomy.

FIG. 4 illustrates another known surgical approach to achieving hemostasis in the presence of PPH. This involves suturing the anterior and posterior major walls of the uterus U together at multiple locations using a square suture configuration, as described in more detail in Cho, J. H., et al., "Instruments & Methods Hemostatic Suturing Technique for Uterine Bleeding During Cesarean Delivery," *Obstetrics & Gynecology*, Vol. 96, No. 1 (July 2000), pp. 129-131. The descriptions in this article of suturing procedures used in the presence of PPH are incorporated herein by reference. A single suture is used for each of two square suture patterns SQ1 and SQ2. As will be appreciated from the figure, each pattern is made by passing the suture through the major uterine walls from anterior to posterior and back again (the portions posteriorly of the uterus are shown in dotted lines) to form a rectangle, with the suture ends tied together at respective knots KN1 and KN2. This also achieves hemostasis—assuming the sutures are placed in the correct locations in the uterus. That is the site of the hemorrhage can be in the upper part of the uterine fundus where the placenta normally attaches, in which case sutures placed as shown in FIG. 4 will be effective in achieving hemostasis. However, the hemorrhage site can also be at a location lower in the fundus of the uterus, in which case suturing at locations such as those shown in FIG. 4 will be ineffective and cause time to be lost before the sutures are applied to the correct location.

In addition to these known surgical techniques for addressing PPH, the prior art includes disclosures of various instruments and devices for the same purpose. One type of known device uses one of more expandable inserts to exert pressure on the uterine walls. Devices implementing this technique basically use two approaches. One involves placing the insert within the uterus and introducing fluid under pressure to expand it against the internal walls of the uterus. This type is exemplified by prior art such as U.S. Pat. No. 6,676,680, U.S. Pat. No. 7,220,252, Chinese Pat. No. CN201055393(Y), Chinese Pat. No. CN202342111(U), Chinese Pat. No. CN202426595(U), and Chinese Pat. No. CN202458535(U). The second approach is exemplified by Pub. No. US2012/0172898, in which hard outer shell halves are placed anteriorly and posteriorly around the uterus and an inflatable bladder associated with each shell half is inflated to press against the exterior of the uterus. Such devices by their nature require some sort of auxiliary mechanism to force fluid under pressure into the expandable insert or bladder. This means that these devices will be costly and also inherently involve a certain amount of complexity in their operation. Although clinically effective inflatable devices that compress the uterine walls from the inside are known in the art, their cost and the necessity for auxiliary operating/control apparatus may make them unattractive or unavailable in less developed countries.

There are other prior art devices that place external pressure on the uterus to achieve hemostasis. U.S. Pat. No. 8,579,925 discloses a clamp with narrow jaws that squeeze the uterus along a transverse line at a lower uterine segment, with a belt that extends between the jaws over the fundus of the uterus. It is not known if this clamp is effective in controlling postpartum hemorrhaging in clinical settings, but it appears to have some shortcomings. For one, it would seem to be unwieldy to maneuver into place, thus costing precious seconds during emergency hemorrhaging. It also has many parts and would likely prove expensive to manufacture, making it less attractive for use in third world countries where the need is the greatest for an inexpensive way of managing PPH. It also uses an elastic belt made of rubber or like material, which would present sterilization issues.

Another proposed uterine clamp has been describe by as design team at the University of Virginia. See https://www.flickr.com/photos/7524869@N02/3295687618/in/photostream. This clamp comprises two plates rigidly mounted parallel to each other on a frame with handles that permit the surgeon to move the plates toward each other to clamp the uterus between them. No reports of experience with this device have been found, but as with the '925 patent clamp, it may also prove to be too unwieldy to provide effective emergency intervention in the presence of PPH. Not only is the handle and cantilevered plate configuration bulky, but the orientation of the plates relative to each other is fixed, thus forcing the surgeon to manipulate the entire clamp assembly into the proper orientation so that the plates are positioned to compress opposing walls of the uterus.

Accordingly, there is unknown in the art a device that can be rapidly and properly positioned on the uterus to achieve immediate hemostasis in the presence of PPH, while being simple in design and inexpensive to manufacture to allow for widespread use in underdeveloped countries in which uterotonic drugs are often unavailable.

Another postpartum issue often faced by the delivering physician is the need to move the postpartum uterus after a C-section to permit repair of uterine trauma resulting from the procedure. For example, a C-section inherently involves an incision IN (see FIGS. 1-3) at the lower uterine segment, and repairing this incision can present challenges to the surgeon because it sometimes requires elevating the exteriorized uterus from the patient's abdomen to minimize possible damage to surrounding organs while performing the necessary repairs. It will be appreciated that a postpartum uterus is covered with blood and other fluids, and as a result is very slippery. In one known technique the physician wraps the uterus in a laparotomy pad to gain a firm grasp on the uterus. However, this may prove awkward in certain situations and for some patients. For example, it can often be difficult to reach and maneuver the uterus of an obese patient into a favorable position to perform a desired postpartum procedure.

SUMMARY OF THE INVENTION

It is an object of the present invention to provide a uterine clamp that can be quickly and easily maneuvered into position to capture and hold a uterus by grasping opposing major walls of the uterus.

One aspect of the invention, broadly stated, is a medical clamp for holding a uterus. The clamp comprises (i) a first plate and a second plate, each having a curved interior major surface for contacting major exterior walls of the uterus, (ii) an operating handle including a first actuating arm and a second actuating arm, each actuating arm including a distal portion and a proximal portion with a grip for a user, wherein the actuating arms are pivotally connected together for moving the distal portions toward each other when the user moves the grips toward each other to capture the uterus between the plates, (iii) a first ball-and-socket joint connecting the distal portion of the first handle to the first plate, and (iv) a second ball-and-socket joint connecting the distal portion of the second handle to the second plate. As the surgeon squeezes the grips together with the uterus between the plates, the major uterine walls are captured between the plates. In one application of the clamp described and claimed herein, the plates can be configured for compressing the uterine walls to rapidly achieve hemostasis in the presence of postpartum hemorrhaging. In another application, the clamp can be used to grasp a uterus that has been exteriorized via laparotomy to manipulate it into a desired position.

In another aspect of the invention, the actuating handle includes a ratcheted lock mechanism for holding the actuating arms in place stepwise against a force tending to separate the distal portions as the grips are moved toward each other. The surgeon can squeeze the grips while the clamp is in place on the uterus, thus maintaining compression on the uterus if it contracts or changes shape while the clamp in place. The lock mechanism holds the plates securely against the uterus as the grips move closer together, thereby maintaining a firm grasp on the uterus without requiring the surgeon to continue squeezing the grips and/or to permit the clamp to be used to manipulate the uterus into as variety of positions during the postpartum phase of delivery while the uterus is held securely between the plates.

Method aspects of the invention involve using the clamp to achieve nearly instantaneous hemostasis while performing other PPH interventions, such as one or more of (i) a B-Lynch procedure as discussed above, (ii) a procedure whereby the major walls of the uterus are sutured together at one or more locations, (iii) arterial ligation, and (iv) the administration of uterotonic drugs, to mention a few examples. In all of these cases the use of a medical clamp as disclosed and claimed herein eliminates the emergency situation surrounding the employment of these known procedures and thus increases the likelihood that they will be successful in achieving permanent hemostasis.

This Summary is provided solely to introduce in a simplified form a selection of concepts that are described in detail further below. It is not intended necessarily to identify key or essential features of the subject claimed herein, nor is it intended to be used an aid in determining the scope of the claimed subject matter.

BRIEF DESCRIPTION OF THE DRAWINGS

Objects of the invention will be better understood from the detailed description of its preferred embodiments which follows below, when taken in conjunction with the accompanying drawings, in which like numerals and letters refer to like features throughout. The following is a brief identification of the drawing figures used in the accompanying detailed description.

Those skilled in the art will readily understand that the drawings omit details of various manners of implementing certain aspects of the invention, but nevertheless will find them sufficient, when taken with the detailed descriptions of preferred embodiments that follow, to make and use the present invention.

DETAILED DESCRIPTION OF PREFERRED EMBODIMENTS

It should be understood that the description herein is intended solely as exemplifying various forms the invention can take. Thus, it will be appreciated that the detailed description that follows is intended solely to provide specific examples of particular embodiments illustrating various ways of implementing the claimed subject matter, and that the invention is defined solely by the claims appended hereto, which are not limited to implementation or realization by any specific embodiment or example used to illustrate certain aspects of the invention. Moreover, the description herein is written to take into account the level of knowledge of one of ordinary skill in the art to which the claimed subject matter pertains. Accordingly, some specifics may be omitted as being unnecessary for enabling such a person to realize the embodiments described herein. It will also be understood that terms indicating direction or orientation, such as "top," "bottom," "upper," "lower," etc., may be used throughout to facilitate the description. The use of such terms does not imply that the claimed subject matter is limited to a particular orientation of the item, structure, or feature being described.

Figure 5:
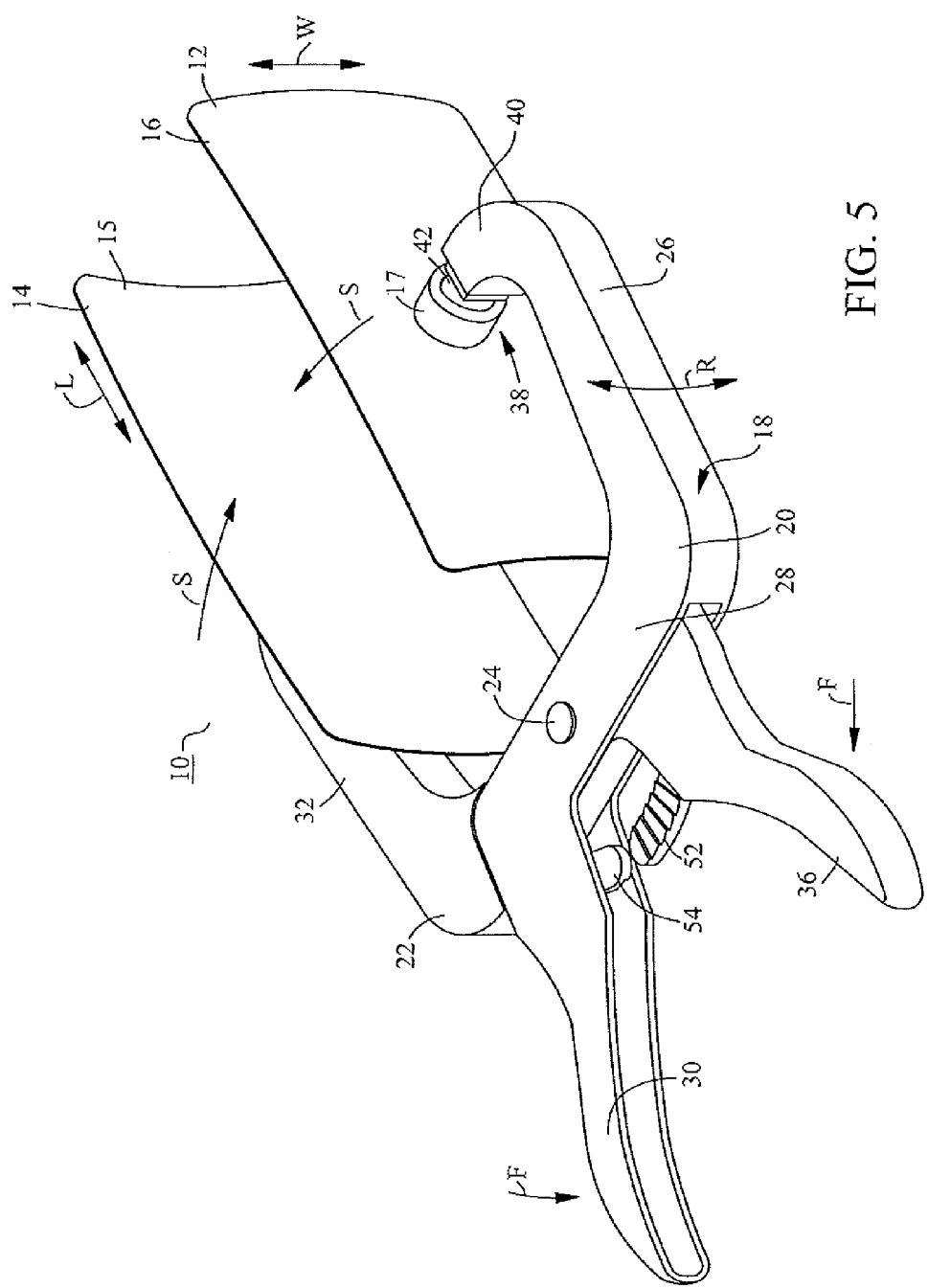
FIG. 5 is an isometric view of an exemplary embodiment of a uterine clamp embodying certain principles of the present invention.

I. Overview of an Embodiment Illustrating General Principles Underlying the Invention FIG. 5 is an isometric view of a first embodiment of a uterine clamp 10 that illustrates basic features of the invention. The clamp 10 includes a first plate 12 and a second plate 14 which in this embodiment are generally rectangular in planform with rounded corners to minimize damage to sensitive adjoining tissue, either of the uterus itself or of surrounding organs. The peripheral edges of the plates will typically be beveled or rounded for the same reason. The dimensions of the plates 12 and 14 approximate the size of a normal uterus of a human female. Typically, the plates are about 10±2 cm wide (in the width direction W) and 15±3 cm long (in the length direction L). In addition, the plates present curved, mutually facing interior major surfaces 15 (only one of which, on the plate 14, is visible in FIG. 5). Those skilled in the art will appreciate that the plates 12 and 14 can have any dimensions and shape suitable for compressing the uterine walls between them, as described in more detail further below, and therefore can be configured in any manner which fulfills that purpose. The plate 12 includes at the approximate center of its external major surface 16 a socket 17 for accepting a ball on an arm of an operating handle 18 in a manner to be described. The external surface of the plate 14, not visible in FIG. 5, includes a similar socket.

The operating handle 18 includes a first actuating arm 20 and a second actuating arm 22 pivotally connected to each other by a pivot pin 24. Particular constructional details of the pivotal connection of the arms 12 and 14 are not part of the invention, and it will be well within the level of ordinary skill of an artisan to implement the pivotal connection between the arms to achieve the ends described herein. In addition, the second actuating arm 22 is only partially visible in FIG. 5, but it will be understood that except in ways specifically mentioned, it is identical to the first actuating area 20, described here in detail. The arm 20 includes a distal portion 26, a lateral portion 28, and a proximal grip 30. The arm 22 includes a similar distal portion 32, lateral portion 34, and proximal grip 36.

The joints between the plates 12,14 and their respective actuating arms 20,22 represent an important aspect of the subject matter claimed as the invention. Reference numeral 38 denotes the joint connecting the first plate 12 and the first actuating area 20. It will be understood that in the present embodiment the joint connecting the second plate 14 and the second actuating arm 22, although not visible in FIG. 5, is identical to the joint 38. More specifically, the distal end 40 of the arm 20 carries a ball 42 that fits within the socket 17 on the plate 12 to form a ball-and-socket joint 38 that permits the first plate 12 to rotate freely relative to the first actuating arm for purposes described in more detail below in connection with the manner in which the clamp 10 is used. Likewise the joint connecting the second plate to its actuating arm permits free rotation of those two components relative to each other.

Stated another way, each joint comprises means for permitting rotation of the plate about three mutually perpendicular axes relative to its corresponding actuating arm. These axes, for example, comprise an axis perpendicular to the external surface of the plate 12, an axis in the length direction L, and an axis in the width direction W. Those skilled in the art will appreciate that any connection between a plate and its respective arm that serves this function is within the scope of the invention. For example, the balls of the ball-and-socket joints could be on the plates, with the sockets on the actuating arms. In another variation, a universal-type joint would comprise a suitable connection between a plate and its respective actuation arm. This is an important aspect of the invention because of the operational advantages it provides, as will be appreciated as the present description proceeds.

Figure 1:
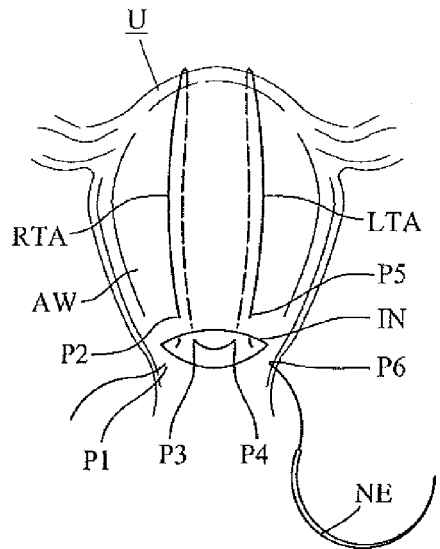
FIGS. 1 to 3 depict one version of the prior art B-Lynch procedure for suturing a uterus to arrest PPH.
Figure 2:
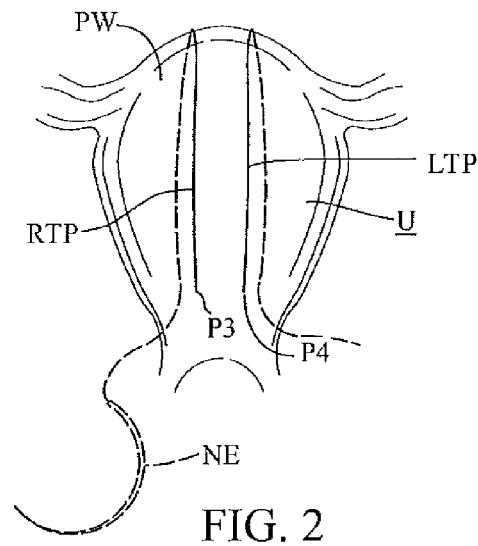

The distal portion 26,32 of each arm 20,22 is oriented generally parallel to the external curved surface of the corresponding plate 12,14, and transitions to the respective lateral portion of each arm 28,34 at a location beyond the edges of the plates 12,14. The clamp is constructed to provide sufficient clearance between the arms' connecting portions and the plates' edges to permit the handle to rotate 360° around the plates in the directions R in FIG. 5. The lateral portions extend transversely to the plates and then transition to the respective grips 30,36, as seen in FIG. 5. In the embodiment shown, the lateral portion 34 of the second arm 22 fits within the lateral portion 28 of the first arm 20. The pivot pin 24 passes through both lateral portions 28,34 at a point approximately midway between the plates 12 and 14. In other words, the lateral portions 28,34 permit the actuating arms to pivot together to move the distal portions toward each other when the user moves the grips toward each other. Thus, applying a force F to the grips 30 and 36 in the direction shown in FIG. 5 squeezes the plates 12 and 14 together in the direction of the arrows S. In this fashion the user can grasp the grips 30 and 36 in one hand, position the plates 12 and 14 against a postpartum uterus's anterior and posterior major exterior walls AW,PW (see FIGS. 1 and 2, for example), and squeeze the grips together to compress the uterine walls and achieve nearly instantaneous hemostasis. In an alternate construction, the plates can be spring-biased apart to facilitate maneuvering them into position facing the major uterine walls. A typical manner of incorporating such a spring bias would be to bias the grips apart. A suitable mechanism of incorporating such a spring bias is well within the ability of those skilled in the art.

A ratcheted lock mechanism holds the grips 30,36, and thus the plates 12,14, in place in stepwise fashion as the user squeezes the grips together. The ratcheted lock mechanism comprises a tongue 52 rigidly connected to the second grip 36 and extending toward the first grip 30 along an arc with a center of curvature at the pivot pin 24, and a cooperating tab 54 rigidly connected to the first grip and extending toward the second grip along the same arc. The upper surface of the tongue 52 has transverse grooves that accept one or more transverse cogs on the lower surface of the tab 54. The grooves have on one side a flat surface that is perpendicular to the direction of relative movement of the tongue and tab, and a sloped surface on the other side of the groove. As the grips are squeezed toward each other, the tab or tabs, which have corresponding perpendicular flat and sloped sides, are cammed from one groove to the next by the cooperating sloped surfaces. The grips are held in place by the facing perpendicular surfaces on the tab(s) and grooves until the grips are squeezed further together. While the presence of a releasable locking mechanism is one aspect of the subject matter claimed herein, its particular structure in any given embodiment can borrow from ratcheted locking mechanisms on known surgical clamps. For example, U.S. Pat. No. 6,099,539, U.S. Pat. No. 6,315,780, and U.S. Pat. No. 8,579,925 all disclose ratcheted locking mechanisms that one skilled in the art would be able to adapt to the principles of the uterine clamp disclosed and claimed herein. The descriptions in these patents of ratcheted locking mechanisms are incorporated herein by reference.

In a preferred implementation, the clamp 10 will be made as a unit. That is, it will be present in a delivery room or operating room as is, without the need for any assembly, so that it is available immediately when the physician or other attending professional realizes the presence of postpartum hemorrhaging. To that end, all of the parts of the clamp 10 will preferably be made of a material that enables sterilization as a unit, which can then be sealed in a suitable package kept at hand for immediate access when needed. Thus, in use, for example when uncontrolled postpartum bleeding is present, the attending obstetrician simply opens the package with the sterilized clamp, positions the uterus between the plates 12,14, and squeezes the grips together to compress the uterus's anterior and posterior major walls together. In addition, multiple clamps 10 with plates 12,14 of various sizes and shapes can be maintained at hand in the delivery room so they are available for different size uteri, or to maintain access to a caesarean incision IN further up on the uterine fundus than is depicted in the drawings herein, or for differing procedures such as those described below in connection with FIGS. 6 to 9.

In the present embodiment the mutually facing interior major surfaces of the plates 12,14 are concave relative to each other with a shallow curvature in the width direction W and the length direction L that approximates the surface curvature of a uterine fundus. In use the surgeon can hold the grips 30,36 in one hand and maneuver the plates in position with the uterus between them so that the length direction L of the plates extends substantially from top to bottom of the fundus of the uterus. The curvature of the plates substantially conforms to the contour of the uterus, so that as the surgeon squeezes the grips, the plates forcibly clamp together the uterine major wall AW and posterior major wall PW. (See FIGS. 1 to 4.) The amount of curvature in the width and length directions is such that the uterus in a central region of the plates is compressed slightly more tightly than at the more peripheral regions of the plates. The curvature also assists in maintaining the plates in position on the uterus by forming a slightly concave enclosure in which the uterus is captured when the plates are squeezed together.

The joints between the respective plates and operating handles allow each plate to orient itself relative to the uterine wall with which it is in contact. This means that the surgeon does not have to spend critical seconds trying to align the uterus and plates rigidly mounted to their handle structure before squeezing the uterus between the plates. Moreover, the rotation about three mutually perpendicular axes permitted by the ball-and-socket joints or their equivalent allows the plates to orient themselves in a manner that captures the uterus in the shallow cavity formed by the complementary concave curvature of the plates and maintains a substantially uniform pressure over the entire surface of the uterine walls as the grips are ratcheted closed. This ensures that hemostasis can be achieved even though the surgeon may not know the exact location within the uterus of the hemorrhage site. In addition, permitting rotation of the operating handle relative to the plates in the directions R both facilitates positioning the clamp and enables the surgeon to maintain the uterus clamped between the plates while he or she accesses different parts of the uterus to effect other interventions with the clamp in place. In a particularly advantageous implementation of the clamp 10, the joints 38 will made so that they present a predetermined amount of resistance to movement about all of the axes of rotation. One way of implementing this construction would be to have the ball fit closely within the socket so that there is a predetermined amount of frictional resistance to relative movement of the ball and socket. The ball and socket surfaces could also be treated in a manner that increases the friction between them, such as by etching or knurling one or both of them. This will keep the plates in desired positions (say generally parallel) relative to each other and to the handle while the surgeon positions them with the uterus therebetween. This will enable even more rapid and convenient deployment of the clamp.

Typical prior art protocols in the presence of postpartum hemorrhage are discussed above and in the medical literature cited there. One such protocol involves the serial administration of a variety of uterotonic drugs. Such a series might involve first an intravenous infusion of oxytocin. If the patient does not respond, the uterus might be packed with gauze or an inflatable member might be inserted into the uterus to compress the interior surfaces of the uterine walls. Other therapies and interventions short of surgery are also possible, but if all fail to achieve hemostasis, resort is normally had to surgical interventions such as ligation of bleeding sites, uterine artery ligation, or B-Lynch or square suturing (as discussed above and shown in FIGS. 1 to 4), or as a last resort, hysterectomy. It will be appreciated that all of these interventions take a certain amount of time, during which the patient may continue to hemorrhage.

The clamp 10 of the present invention permits a particular intervention protocol to be employed without the urgency attendant if the patient continues to hemorrhage while successive stages of the protocol are employed. The clamp can be used to that end in accordance with the following exemplary revised protocol. If the uterus is already exposed as a result of a caesarean delivery, the clamp 10 can be placed into position nearly instantly with the uterus between the plates 12, 14 and hemostasis achieved immediately by squeezing the grips 30,36 together in stepwise fashion as the cogs on the tab 54 advance from groove to groove on the tongue 52. Otherwise, a laparotomy is performed to expose the uterus. Either way, the ball-and socket joints connecting the actuating arms 20,22, to the plates 12,14 permit the surgeon to position the plates without requiring him or her to move into a particular position relative to the patient, or alternatively, to manipulate the uterus into a particular orientation. As already discussed, when the plates are in place the ball-and-socket joints permit them to automatically orient themselves relative to the anterior and posterior major exterior walls of the uterus to achieve compression over a substantial portion of the walls. This is in contrast to prior art structures such as the belted clamping device described in U.S. Pat. No. 8,579,925, which requires two hands to apply compression to the uterus. It also improves over the above-described University of Virginia clamping device, in which the plates do not move relative to the actuating mechanism operated by the surgeon and thus requires that the device be bodily moved to achieve uniform compressive pressure over the surfaces of the uterus. Another advantage of a clamp in accordance with the principles and construction described herein is that the uterus can be more readily manipulated to be between the plates 12,14 in obese patients, whose uteri can be difficult to access, particularly so with prior art clamping devices such as the University of Virginia clamp or the device described in the '925 patent. In addition, the clamp 10 does not require the presence of an assistant, since the surgeon can squeeze the grips with one hand to move the plates, and manipulate the uterus as required with the other hand.

The clamp 10 can be applied before or after the administration of uterotonic drugs. Although postpartum protocols typically involve routine administration of uterotonic drugs such as Pitocin® (oxytocin injection), if the use of such drugs is contraindicated in a particular patient (because of drug allergies, for example), the clamp 10 would be a valuable alternative. Particularly in the case of a caesarean delivery and the speed with which the clamp 10 can be applied, the surgeon might decide to use the clamp on the already exposed uterus as a precautionary measure in conjunction with a uterotonic drug, in the event the patient does not respond to the drug therapy. This would achieve substantially instantaneous hemostasis and thus prevent the blood loss that would otherwise occur while waiting to see if the drug therapy is effective. The clamp disclosed and claimed herein enables the surgeon to intermittently or continuously squeeze the grips to maintain compression on the uterus if it contracts or changes shape as the uterotonic drugs take effect. In a vaginal delivery the surgeon might prefer to wait before performing the laparotomy that would be necessary anyway to employ prior art surgical interventions. And in locations where drug therapies are not available, such as less developed countries, the clamp that is disclosed and claimed herein can be used to achieve hemostasis in time to save lives that might otherwise be lost because of delays in achieving hemostasis, or to reduce the number of hysterectomies performed to stop hemorrhaging.

Those skilled in the art will recognize that alternate constructions of the clamp 10 are possible within the scope of the claimed invention. For example, the rectangular plates 12,14 can have other shapes. In addition, the plates 12,14 in the present embodiment are curved in both the longitudinal direction L and the width direction W, or but they could have a more complex topology to inure closely match that of the uterus. Nor does the curvature of the plates have to be a segment of a circular arc, but can be elliptical or other shapes. The salient property provided by the curvature of the plates is to compress together substantial portions of the major uterine exterior walls and capture and hold the uterus in the concave space created by the curvature of the plates. Suitable contours will be readily determined by those skilled in the art in accordance with the description herein of the manner of using the device.

Although the utility of a clamp as disclosed and claimed herein described herein for treating PPH is important, because of its potential to save lives and obviate more radical therapies such as hysterectomy, the clamp of the present invention is also useful for more routine postpartum uterine repairs. Since PPH occurs in relatively few deliveries, using the present clamp in other situations will make it more attractive as a standard appliance in delivery rooms, thus ensuring its availability if PPH does occur. In addition, routine usage of the clamp for other purposes will foster familiarity with it as an instrument and thus ensure its proper and rapid deployment in the presence of emergency PPH. Moreover, it facilitates other known postpartum procedures and interventions because the plates 12,14 grasp a substantial area of the uterine walls and enable the surgeon to safely maneuver the uterus to desired positions using the handle because of the arms' multiple-degree-of-rotation mounting to the plates and the secure clamping provided by the ratchet lock mechanism. For example, after a caesarean delivery, suturing the C-section incision can be performed more readily if the exteriorized uterus s elevated from the patient's abdomen in order to avoid to the greatest extent possible damage to surrounding organs such as the bladder. Typically, the surgeon wraps the uterus with laparotomy pad and carefully elevates it by hand. However, a clamp as disclosed and claimed herein will allow the surgeon to secure the exteriorized uterus between the plates 12,14 and use the rotatable handle 18 to move the uterus into desired locations and orientations that will minimize potential damage to the uterus and surrounding organs as the uterine trauma is treated. One routine application of the clamp's ability to readily hold the uterus in a desired orientation and location would enable more ready access and repair of uterine trauma caused by caesarean deliveries, such as repairing C-section incisions, including the often difficult to reach extreme ends of a wider than normal incision. But this capability of the clamp is also important for other known PPH interventions, such as safely and quickly moving the uterus into a position that will protect surrounding organs from damage while performing uterine artery ligation (see O'Leary), J. L., et al., "Uterine Artery Ligation in the Control of Intractable Postpartum Hemorrhaging," *American Jour. of Obstetrics & Gynecology*, above).

II. Second Embodiment Having Enhanced Clamping Capabilities

Figure 6:
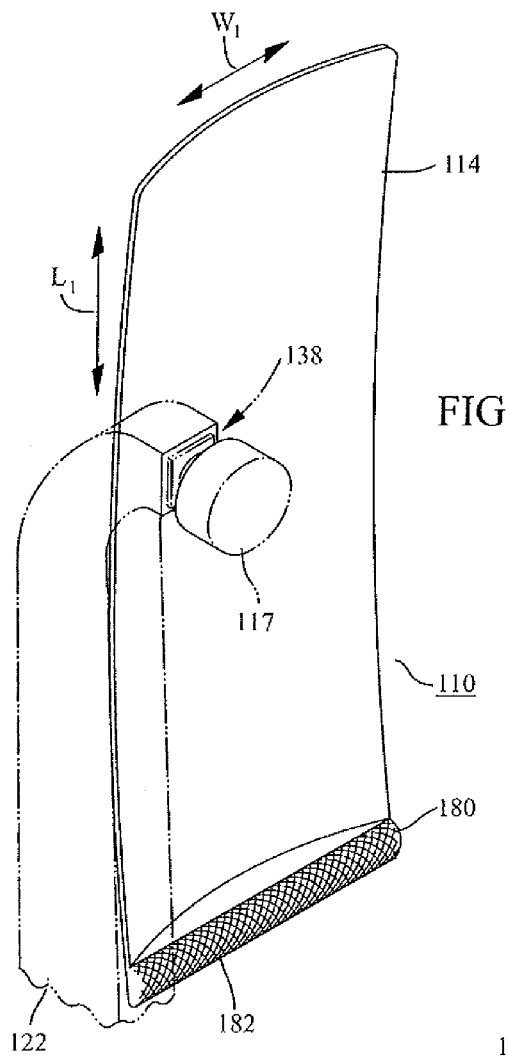
FIG. 6 is an isometric view illustrating an alternate embodiment of the uterine clamp depicted in FIG. 5.
Figure 7:
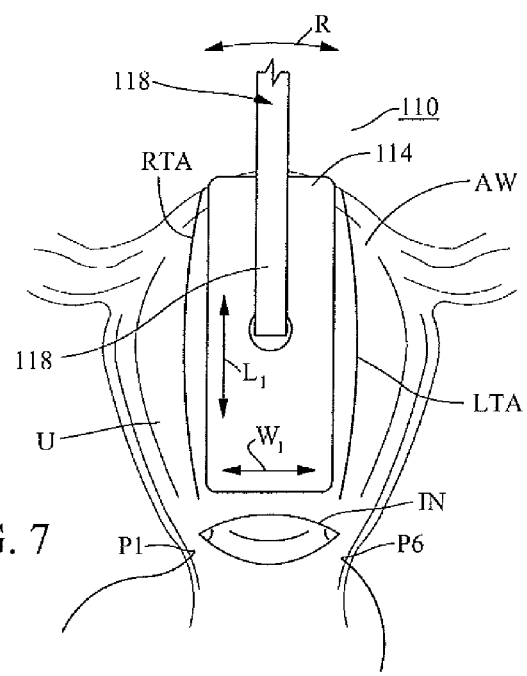
FIG. 7 is a plan view showing the clamp embodiment of FIG. 6 used in conjunction with the prior art B-Lynch procedure shown in FIGS. 1 to 3.

A clamp in accordance with the present invention can also include additional features for enhancing its capabilities for facilitating routine postpartum uterine repairs and for other known PPH treatment interventions, such as a B-Lynch procedure, that require access to the posterior uterine wall to implement. FIGS. 6 and 7 illustrate an alternate embodiment of a clamp particularly adapted for that purpose. FIGS. 6 and 7 use the same reference numerals as the previous embodiments for similar features, except that they have a "1" preceding them. In other words, a clamp 110 in FIGS. 6 and 7 represents a second embodiment of the clamp 10 depicted and described above, with the same features, except where explicitly stated otherwise or as will be apparent as the description proceeds. As used herein, "B-Lynch procedure" means the procedure described in connection with FIGS. 1 to 3 above or variations thereof described in the literature, including the articles incorporated by reference herein.

Figure 3:
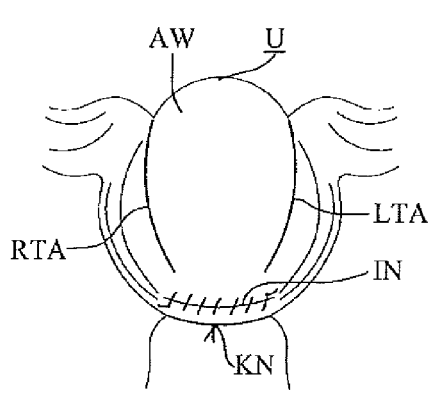
Figure 4:
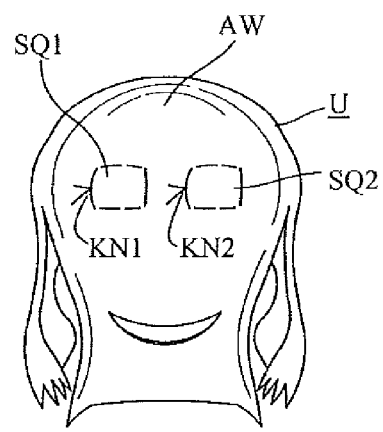
FIG. 4 depicts a prior art square suture technique that sutures together opposing major walls of the uterus to arrest PPH.

In that connection, FIG. 6 is an isometric view of a plate 114 and its corresponding actuating arm 120 of the clamp 110. It will be understood that the clamp 110 also includes another plate (not shown) that is similar to the plate 114 in the same fashion that the plate 12 is similar to the plate 14 in the FIG. 5 embodiment. The actuating arm 122 is connected to the external major surface of the plate 114 by a ball-and-socket joint 138 corresponding to the joint 38 described above. As before, the joint 138 performs the same functions as in the previously described embodiment and can be replaced by equivalent structure in the manner described. FIG. 7 depicts the clamp 110 in place on a uterus U which has been subjected to a B-Lynch procedure (here the procedure described above in connection with FIGS. 1 to 3). In accordance with the present embodiment, FIG. 7 shows that the dimension of each plate in the length direction $L_1$ spans the uterus substantially from the top to the bottom of the uterine fundus, while in the width direction $W_1$ each plate exposes a predetermined amount of the peripheral sides of the uterus to enable the surgeon to effect a B-Lynch procedure of his or her choice. Accordingly, immediate hemostasis can be achieved using the clamp 110, thus eliminating the emergency condition presented by hemorrhaging and permitting the surgeon to carefully complete a B-Lynch procedure to achieve long-term hemostasis. That is, with the clamp 110 in place as shown in FIG. 7 to achieve temporary hemostasis, the surgeon can perform a B-Lynch procedure. The clamp 110 also further simplifies the procedure by eliminating the need to have an assistant compress the uterus while the suture is drawn tight to compress the uterine walls. The clamp 110 can then be removed once the B-Lynch suture is in place as shown in FIG. 3. It will also be appreciated that the ability to rotate the operating handle 118 in the directions R, as shown in FIGS. 5 and 7, enables the surgeon to move the handle into various positions as be or she manipulates the uterus, especially in connection with procedures such as elevating the uterus or B-Lynch suturing.

FIG. 6 depicts another feature of the invention in which a raised knurled gripping portion 180 spans the proximal edge of the plate 114 in the width direction. In embodiments with this gripping portion, it will typically be included on both plates in facing relation (that is, generally in the same location on both plates) to provide additional traction between the plates and the uterus to while the surgeon is manipulating the uterus in connection with any of the procedures or uterine repairs described herein. The facing raised gripping portions 180 on the plates 114 and 116 (or 14 and 16 in the case of the clamp 10 shown in FIG. 5) apply additional gripping force to the lower region of the uterine fundus, which is typically thinner in the anterior-posterior direction than regions higher up in the fundus. The edges of the gripping portion 180 are rounded to prevent tissue damage and present a substantially flat surface 182 that will cooperate with the corresponding flat gripping portion on the other plate to more tightly clamp the lower fundus of the uterus between the gripping portions. The optional knurling on the surface 182 provides even more traction with the surface of the uterus, which, as noted above, will be covered in blood and amniotic fluid after delivery. In a variation of this embodiment the gripping surface could be slightly concave, which will minimize the possibility of subjecting the uterus to excessive compression by the gripping portions. In a preferred embodiment of this variation the curvature of the gripping portions will be slightly less than the curvature of the contiguous plate edge to ensure that they firmly grasp the uterus. It will also be appreciated that similar gripping portions can be included along one or both edges of the plates in the length direction, as well as or instead of the gripping portion on the widthwise edge as shown in FIG. 6.

III. Third Embodiment Permitting Use of Square Suturing Techniques

Figure 8:
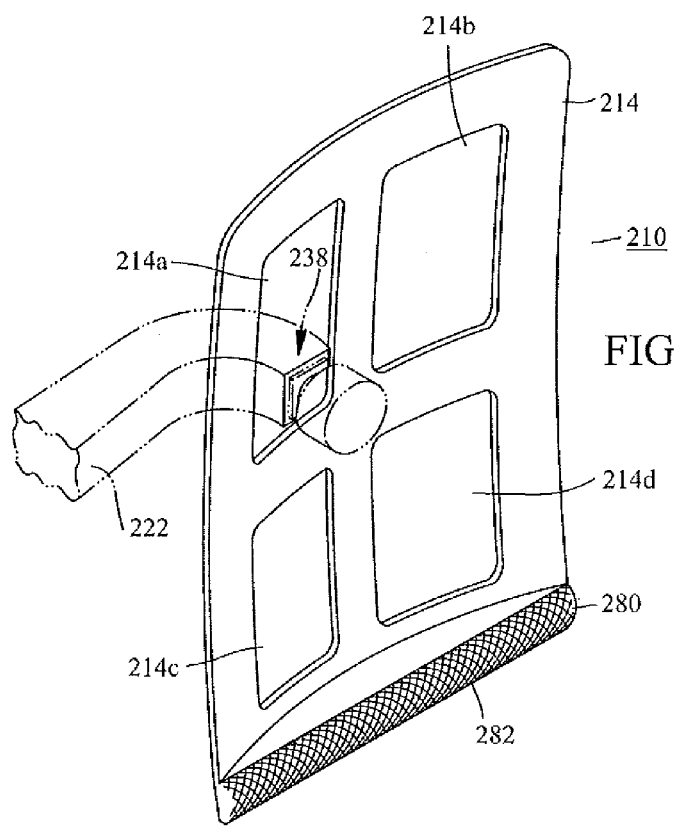
FIG. 8 is an isometric view illustrating another alternate embodiment of the uterine clamp depicted in FIG. 5.
Figure 9:
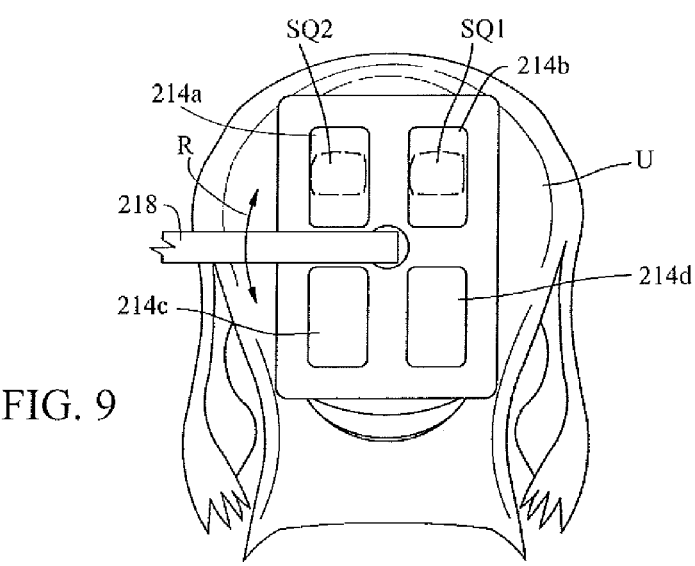
FIG. 9 is a plan view showing the clamp embodiment of FIG. 8 used in conjunction with the prior art square suture procedure shown in FIG. 4.

A uterine clamp according to the principles described herein can be used in conjunction with other known PPH interventions to mitigate the emergency conditions under which such interventions heretofore have taken place. The embodiment of FIG. 6, discussed above, makes it possible to perform the more permanent B-Lynch procedure under more controlled conditions rather than as part of an emergency response. That is, while a clamp as described and claimed herein may in itself promote permanent hemostasis, it has the added advantage of permitting the employment of more permanent interventions while remaining in place. For example, a clamp in accordance with the present invention can also be adapted to permit the use of procedures in which the major uterine walls are sutured together, such as the square suturing techniques described above in conjunction with FIG. 4, FIGS. 8 and 9 illustrate a third embodiment of a clamp particularly adapted for that purpose. FIGS. 8 and 9 use the same reference numerals as the previous embodiments for similar features, except that they have a "2" preceding them. In other words, a clamp 210 in FIGS. 8 and 9 represents a third embodiment of the clamp 10 depicted and described above, with the same features, except where explicitly stated otherwise or as will be apparent as the description proceeds.

In that connection, FIG. 8 is an isometric view of a plate 214 and its corresponding actuating arm 222 of the clamp 210. It will be understood that the clamp 110 also includes another plate (not shown) that is similar to the plate 114 in the same fashion that the plate 12 is similar to the plate 14 in the FIG. 5 embodiment. The actuating arm 222 is connected to the external major surface of the plate 214 by a ball-and-socket joint 238 corresponding to the joint 38 described above. As before, the joint 238 serves the same function as in the previously described embodiment and can be replaced by equivalent structure in the manner described. The plate 214 is generally rectangular with four cutouts 214a, 214b, 214c, and 124d in each quadrant of the rectangle formed by the plate 214. FIG. 9 depicts the clamp 210 in place on a uterus U which has been subjected to a square suturing technique as described above in connection with FIG. 4 in each of the cutouts 214a and 214b. It will be appreciated that if the locus of the PPH is lower in the uterine fundus, the square suturing can be performed in one or both of the cutouts 214c and 214d. As with the other embodiments described herein, the dimensions and shapes of the plates are chosen to suit the purpose for which the clamp is to be used. In the case of the present embodiment, it may be desirable to have in the delivery room a variety of shapes and sizes, with cutouts located in different areas, to provide the surgeon with a choice as to which is best suited to a particular case at hand. As in the other instances described herein, immediate hemostasis can be achieved using the clamp 210, thus eliminating the emergency condition presented by hemorrhaging and permitting the surgeon to carefully complete one or more square sutures while the walls of the uterus are maintained stationary and PPH is arrested. That is, with the clamp 210 in place, as shown in FIG. 9, the surgeon can perform a suturing technique that secures the uterine walls together as described above in connection with FIG. 4, or variations thereof described in the publications cited above, after hemorrhaging has been arrested. The clamp 110 also assists in performing such techniques because the uterine walls are maintained in contact while the procedure is performed. The clamp 210 is then removed once uterine walls are sutured together. The clamp 210 also includes gripping portions 280 with knurled surfaces 282, corresponding in structure and function to the gripping portions discussed above in connection with FIG. 6.

As in the previous embodiments, the operating handle 218 of this embodiment is rotatable in the directions R in order to facilitate safe manipulation of the uterus while different procedures are performed. In another variation, the joints 38 (138,238) can also have predetermined stops that hold the handles in a particular location against a certain amount of resistance. One manner of realizing this feature would use a detent mechanism that holds the handles at 12:00 o'clock (shown in FIG. 7), 3:00 o'clock, and 9:00 o'clock shown in FIG. 9) until a predetermined force is exerted to move the handle from the detent location. This would even more positively hold the handle in a particular position without requiring a conscious effort on the part of the surgeon to do so, while still allowing the handle to be rotated into another position when desired.

IV. Summary and Conclusion

A uterine clamp in accordance with the constructions and principles described herein can save lives, particularly in areas of the world where drug therapy for PPH is not widely available. It provides an inexpensive solution to a serious health problem and eliminates the emergency and panic aspects attendant to the use of known surgical interventions for PPH. A uterine clamp as disclosed and claimed herein can also facilitate the performance of a variety of postpartum procedures by enabling an attending obstetrician to grip a postpartum uterus that is covered with bodily fluids making it difficult to hold securely.

Those skilled in the art will readily recognize that only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A medical clamp for holding a uterus, the clamp comprising:
   a first plate and a second plate, each having an interior major surface for contacting respective major exterior walls of the uterus;
   an operating handle including a first actuating arm and a second actuating arm, each actuating arm including a distal portion and a proximal portion, wherein the actuating arms are connected together for moving the distal portions toward each other to capture the uterus between the plates when a user operates the proximal portions;
   a first ball-and-socket joint connecting the distal portion of the first handle to the first plate; and
   a second ball-and-socket joint connecting the distal portion of the second handle to the second plate.

2. A clamp as in claim 1, wherein each of the first and second plates has a rectangular planform with an interior major surface and an exterior major surface.

3. A clamp as in claim 2, wherein the plates are curved in at least one of the length and width directions of the rectangular planform.

4. A clamp as in claim 2, wherein the plates are between 8 and 12 cm in the width direction of the rectangular planform and between 12 and 18 cm in the length direction of the rectangular planform.

5. A clamp as in claim 2, wherein the plates have a dimension in the length direction of the planform that spans the uterus substantially from the top to the bottom of the fundus of the uterus and a dimension in the width direction that exposes a predetermined amount of the peripheral sides of the fundus of the uterus.

6. A clamp as in claim 5, wherein the plates are between 12 and 18 cm in the length direction of the rectangular planform.

7. A clamp as in claim 1, wherein at least one of the first and second plates includes on an interior surface thereof at least one gripping portion having a surface raised from the adjoining interior surface of the plate.

8. A clamp as in claim 7, wherein each plate has a rectangular planform and the at least one gripping portion extends in the width direction of the rectangular planform.

9. A clamp as in claim 8, wherein the gripping portions present mutually facing flat surfaces.

10. A clamp as in claim 8, wherein the gripping portion spans substantially the entire width of the plate.

11. A clamp as in claim 8, wherein the at least one gripping portion is disposed proximate to an edge of the plate.

12. A clamp as in claim 7, wherein the gripping portion presents a flat surface facing the other of the first and second plates.

13. A clamp as in claim 7, wherein the first and second plates each include on an interior surface thereof at least one gripping portion facing the other plate.

14. A clamp as in claim 1, wherein:
   the proximal portion of each actuating arm includes a grip for the user;
   the actuating arms are pivotally connected together for moving the distal portions toward each other when the user moves the grips toward each other; and
   the operating handle includes a lock for holding the actuating arms in place against a force tending to separate the distal portions as the grips are moved toward each other.

15. A clamp as in claim 14, wherein the lock includes a ratcheted mechanism for holding the actuating arms in place stepwise against the force tending to separate the distal portions.

16. A clamp as in claim 15, wherein the actuating arms are spring-biased in a direction tending to force the plates away from each other.

17. A clamp as in claim 1, wherein the ball-and-socket joints present a predetermined amount of resistance to movement of the plates relative to the actuating arms.

18. A clamp as in claim 17, wherein the ball of each ball-and-socket joint fits closely within its corresponding socket to present frictional resistance to relative movement of the ball and socket.

19. A clamp as in claim 1, wherein the first and second plates are substantially identical with a rectangular planform, each having an interior major surface and an exterior major surface with a dimension in the length direction that spans the uterus substantially from the top to the bottom of the fundus of the uterus and a dimension in the width direction that exposes a predetermined amount of the peripheral sides of the uterus to enable the B-Lynch procedure to be performed.

20. A clamp as in claim 1, wherein the plates are dimensioned to substantially cover the exterior walls of the uterus and the plates include corresponding cutout regions for permitting access to the opposing major uterine walls to permit them to be sutured together with the plates in place on the uterine walls.

21. A clamp as in claim 20, wherein the first and second plates are substantially identical with a rectangular planform, each having four corresponding cutout regions in respective quadrants of the rectangular planforms.

22. A medical clamp for holding a uterus, the clamp comprising:
   a first plate and a second plate, each having an interior major surface for contacting respective major exterior walls of the uterus;
   an operating handle including a first actuating arm and a second actuating arm, each actuating arm including a distal portion and a proximal portion, wherein the actuating arms are connected together for moving the distal portions toward each other to capture the uterus between the plates when a user operates the proximal portions;

a first joint connecting the distal portion of the first handle to the first plate, the first joint comprising means for enabling the first plate to rotate freely relative to the first handle about three mutually perpendicular axes of rotation; and a second joint connecting the distal portion of the second handle to the second plate, the second joint comprising means for enabling the second plate to rotate freely relative to the second handle about three mutually perpendicular axes of rotation.

23. A clamp as in claim 22, wherein the first and second plates have rectangular planforms and are curved in at least one of the length and width directions of the rectangular planform.

24. A method of treating a hemorrhaging uterus, the method comprising:

obtaining a medical clamp including (i) a first plate and a second plate, each having an interior major surface for contacting respective major exterior walls of the uterus, (ii) an operating handle including a first actuating arm and a second actuating arm, each actuating arm including a distal portion and a proximal portion, wherein the actuating arms are connected together for moving the distal portions toward each other to capture the uterus between the plates when a user operates the proximal portions, (iii) a first ball-and-socket joint connecting the distal portion of the first handle to the first plate and a second ball-and-socket joint connecting the distal portion of the second handle to the second plate, and (iv) a lock for holding the actuating arms in place against a force tending to separate the distal portions;

manipulating the first and second plates into position with the major exterior walls of the uterus facing respective first and second plates;

operating the proximal portions to move the plates to compress the uterine walls together; and using the lock mechanism to lock the actuating arms into a clamping position in which the plates exert pressure on the uterus.

25. A method as in claim 24, further comprising:

performing a further procedure to promote permanent hemostasis, the further procedure including at least one of (i) administering at least one uterotonic drug, (ii) performing a B-Lynch procedure, (iii) suturing the walls of the uterus together in at least one location, and (iv) arterial ligation; and removing the clamp from the uterus.

26. A method as in claim 24, further including maintaining the actuating arms in the clamping position to promote hemostasis of the hemorrhaging uterus.

27. A method of performing a postpartum medical procedure on a uterus, the method comprising:

obtaining a medical clamp including (i) a first plate and a second plate, each having an interior major surface for contacting respective major exterior walls of the uterus, (ii) an operating handle including a first actuating arm and a second actuating arm, each actuating arm including a distal portion and a proximal portion, wherein the actuating arms are connected together for moving the distal portions toward each other to capture the uterus between the plates when a user operates the proximal portions, (iii) a first ball-and-socket joint connecting the distal portion of the first handle to the first plate and a second ball-and-socket joint connecting the distal portion of the second handle to the second plate, and (iv) a lock for holding the actuating arms in place against force tending to separate the distal portions;

manipulating the first and second plates into position with the major exterior walls of the uterus facing respective first and second plates;

operating the proximal portions to move the plates to compress the uterine walls together;

locking the actuating arms into a clamping position which the uterus is held between the plates; and using the operating handle to maneuver the uterus into a position for minimizing tissue damage during at least one of an arterial ligation, repair of post-caesarean uterine trauma, and repair of a caesarean section incision.

* * * * *